US005798375A

United States Patent [19]
Tsujita et al.

[11] Patent Number: 5,798,375
[45] Date of Patent: Aug. 25, 1998

[54] TREATMENT OF ARTERIOSCLEROSIS AND XANTHOMA

[75] Inventors: Yoshio Tsujita, Tokyo; Hiroyoshi Horikoshi; Takashi Ito, both of Kobe, all of Japan

[73] Assignee: Sankyo Company, Limited, Tokyo, Japan

[21] Appl. No.: 676,090

[22] Filed: Jul. 2, 1996

[30] Foreign Application Priority Data

Jul. 3, 1995 [JP] Japan ................................ 7-167291

[51] Int. Cl.$^6$ .................... A61K 31/425; A61K 31/21
[52] U.S. Cl. .................... 514/369; 514/370; 514/510
[58] Field of Search ......................... 514/369, 320, 514/310

[56] References Cited

U.S. PATENT DOCUMENTS

| | | | |
|---|---|---|---|
| 4,287,200 | 9/1981 | Kawamatsu et al. | 424/470 |
| 4,340,605 | 7/1982 | Kawamatsu et al. | 424/263 |
| 4,346,227 | 8/1982 | Terehara et al. | 568/119 |
| 4,438,141 | 3/1984 | Kawamatsu et al. | 424/248.51 |
| 4,444,779 | 4/1984 | Kawamatsu et al. | 424/263 |
| 4,448,979 | 5/1984 | Terahara et al. | 549/282 |
| 4,461,902 | 7/1984 | Kawamatsu et al. | 548/183 |
| 4,572,912 | 2/1986 | Yoshioka et al. | 514/369 |
| 4,687,777 | 8/1987 | Meguro et al. | 514/342 |
| 4,703,052 | 10/1987 | Eggler et al. | 514/337 |
| 4,725,610 | 2/1988 | Meguro et al. | 514/369 |
| 4,739,073 | 4/1988 | Kathawala | 548/406 |
| 4,873,255 | 10/1989 | Yoshioka et al. | 514/369 |
| 4,897,393 | 1/1990 | Iijima et al. | 514/233 |
| 4,897,405 | 1/1990 | Alessi et al. | 514/360 |
| 4,918,091 | 4/1990 | Cantello et al. | 514/369 |
| 4,948,900 | 8/1990 | Iijima et al. | 548/183 |
| 5,002,953 | 3/1991 | Hindley | 514/275 |
| 5,006,530 | 4/1991 | Angerbauer et al. | 514/277 |
| 5,061,717 | 10/1991 | Clark et al. | 514/342 |
| 5,120,754 | 6/1992 | Clark et al. | 514/342 |
| 5,132,317 | 7/1992 | Cantello et al. | 514/369 |
| 5,169,857 | 12/1992 | Angerbauer et al. | 514/344 |
| 5,194,443 | 3/1993 | Hindley | 514/367 |
| 5,223,522 | 6/1993 | Clark et al. | 514/369 |
| 5,232,925 | 8/1993 | Hindley | 514/272 |
| 5,260,445 | 11/1993 | Hindley | 548/183 |
| 5,273,995 | 12/1993 | Roth | 514/422 |
| 5,401,746 | 3/1995 | Angerbauer et al. | 514/344 |

FOREIGN PATENT DOCUMENTS

| | | |
|---|---|---|
| 0 022 478 | 1/1981 | European Pat. Off. |
| 0 033 538 | 11/1985 | European Pat. Off. |
| A 0 671 171 | 9/1995 | European Pat. Off. |
| 0 676 398 | 10/1995 | European Pat. Off. |
| 0 708 098 | 4/1996 | European Pat. Off. |
| 5-69383 | 3/1992 | Japan |
| 5-202042 | 8/1993 | Japan |
| 7-41423 | 2/1995 | Japan |
| WO 89/08651 | 9/1989 | WIPO |
| WO 91/07107 | 5/1991 | WIPO |
| WO 92/02520 | 2/1992 | WIPO |
| WO 94/01433 | 1/1994 | WIPO |

OTHER PUBLICATIONS

Yoshio Watanabe et al. "Preventive effect of pravastatin sodium. a potent inhibitor of 3-hydroxy-3-methylglutaryl coenzyme A reductase. on coronary atherosclerosis and xanthoma in WHHL rabbits". Biochimica et Biophysica Acta. 960 (1988). pp. 294–302.

Masashi Shiomi et al. "Suppression of established atherosclerosis and xanthomas in mature WHHL rabbits by keeping their serum cholesterol levls extremely low". Atherosclerosis. 83 (1990). pp. 69–80.

J. Otto et al. "Lovastatin inhibits diet induced atherosclerosis in F1B Golden Syrian hamsters". Atherosclerosis. 114 (1995). pp. 19–28.

T.A. Kotchen. "Attenuation of Experimental Hypertension with Agents That Increase Insulin Sensitivity". DRUG DEVELOPMENT RES.. vol. 32. 1994. pp. 100–103, XP000603648.

J. Clinical Therapeutics & Medicines. 9. Suppl. 3. 19–37, (1993). English translation attached.

J. Clinical Therapeutics & Medicines. 9. Suppl. 3. 151–164, (1993). English translation attached.

Clinic All-round 43. 2615–2621 (1994). English translation attached.

*Primary Examiner*—Theodore J. Criares
*Attorney, Agent, or Firm*—Frishauf, Holtz, Goodman, Langer & Chick, Esq.

[57] ABSTRACT

A combination of one or more HMG-CoA reductase inhibitors (for example pravastatin. lovastatin. simvastatin, fluvastatin. rivastatin or atorvastatin) with one or more insulin sensitizers (for example troglitazone. pioglitazone, englitazone. BRL-49653. 5-(4-{2-[1-(4-2'-pyridylphenyl) ethylideneaminooxy]-ethoxy}benzyl)thiazolidine-2,4-dione. 5-{4-(5-methoxy-3-methylimidazo[5,4-b]pyridin-2-yl-methoxy)benzyl}thiazolidine-2,4-dione or its hydrochloride, 5-[4-(6-methoxy-1-methylbenzimidazol-2-ylmethoxy)benzyl]thiazolidine-2,4-dione, 5-[4-(1-methylbenzimidazol-2-ylmethoxy)benzyl]-thiazolidine-2,4-dione and 5-[4-(5-hydroxy-1,4,6,7-tetramethylbenzimidazol-2-ylmethoxy)benzyl]thiazolidine-2,4-dione) exhibits a synergistic effect and is significantly better at preventing and/or treating arteriosclerosis and/or xanthoma than is either of the components of the combination alone.

6 Claims, No Drawings

TREATMENT OF ARTERIOSCLEROSIS AND XANTHOMA

BACKGROUND OF THE INVENTION

The present invention relates to methods and compositions for the treatment and prophylaxis of arteriosclerosis and/or xanthoma.

Throughout the world, in recent years, the tendency has been for the incidence of coronary artery disease and arteriosclerosis, including atherosclerosis, to increase, even in those countries in which hitherto they have not been prevalent. Amongst the factors implicated in such an increase are changes in lifestyle, including the "Western" meat-rich diet, and the adoption of such a diet even in countries where it is not traditional, and the general increase in the average age of the population. As a result, these diseases and arteriosclerosis, in particular, are widely feared as arteriosclerosis is a well known potential cause of unexpected death, for example by such sequelae of arteriosclerosis as myocardial infarction.

One of the main risk factors implicated in these diseases is a high blood plasma lipid level, particularly a high blood plasma cholesterol level. There have, therefore, been many attempts to use an agent which lowers the cholesterol level in order to prevent and cure these diseases, and many compounds have been developed which, to a greater or lesser extent, have this effect. For example, one such compound, which has been very successful and is very well known is pravastatin, which is a lipid regulating agent and is an inhibitor of 3-hydroxy-3-methylglutaryl-coenzyme A reductase (hereinafter referred to as "HMG-CoA reductase inhibitor") which is believed to act on the rate-determining step of cholesterol biosynthesis. It has been reported that coronary arteriosclerosis and xanthoma may be prevented in rabbits receiving pravastatin, but its efficacy remains insufficient [Biochimica et Biophysica Acta, 960, 294–302 (1988)]. Studies to control coronary arteriosclerosis and xanthoma have been carried out using a combination of two lipid regulating agents, pravastatin and cholestyramine, which is well known as an agent for lowering lipoprotein levels, but the efficacy of this combination also remains insufficient [Atherosclerosis, 83, 69–80 (1990)].

It has been proposed in Japanese Patent Kokai Application No. Hei 7-41423 that a specific class of insulin resistance-improving agents, for example troglitazone, may be effective in the treatment and prophylaxis of arteriosclerosis, particularly atherosclerosis, but, again, the efficacy of such compounds is not quite satisfactory.

BRIEF SUMMARY OF INVENTION

We have now surprisingly found that the application of a combination of one or more HMG-CoA reductase inhibitors with one or more insulin sensitizers exhibits a synergistic effect and is significantly better at preventing and/or treating arteriosclerosis and/or xanthoma than is either of the components of the combination alone. Indeed, employing the new combination of the present invention, these diseases may be slowly but steadily curable.

It is therefore an object of the present invention to provide a combination of one or more HMG-CoA reductase inhibitors with one or more insulin sensitizers or insulin resistance-improving agents.

It is a further, and more specific object of the invention to provide such a combination exhibiting a synergistic effect.

It is a still further object of the invention to provide methods and compositions using such a combination for the prevention and/or treatment of arteriosclerosis and/or xanthoma.

Other objects and advantages of the present invention will become apparent as the description proceeds.

Thus, in a first aspect, the present invention consists in a method for the prevention or treatment of arteriosclerosis or xanthoma, which method comprises administering to a patient suffering from or susceptible to arteriosclerosis or xanthoma a first agent selected from the group consisting of HMG-CoA reductase inhibitors and a second agent selected from the group consisting of insulin sensitizers, said first and second agents being administered together or within such a period as to act synergistically together.

The invention also provides a packaged pharmaceutical formulation for the treatment or prophylaxis of arteriosclerosis or xanthoma, comprising a first agent selected from the group consisting of HMG-CoA reductase inhibitors and a second agent selected from the group consisting of insulin sensitizers, said first and second agents being in admixture or packaged separately.

In a still further aspect, the invention provides a pharmaceutical composition for the treatment or prophylaxis of arteriosclerosis or xanthoma, comprising a first agent selected from the group consisting of HMG-CoA reductase inhibitors and a second agent selected from the group consisting of insulin sensitizers.

DETAILED DESCRIPTION OF INVENTION

At present, the experimental evidence seems to us to suggest that the synergistic effect arises from an interaction between the modes of action of the two classes of compounds, the HMG-CoA reductase inhibitors and the insulin sensitizers, and so the chemical structure of the compounds is believed to be of less importance than their activities. Accordingly, any compound having HMG-CoA reductase inhibitory activity may be used as the first agent, whilst any compound having insulin sensitizing activity may be used as the second agent.

The HMG-CoA reductase inhibitors are commonly used for the treatment or prophylaxis of hyperlipemia, and may comprise naturally occurring substances which originate in the metabolism of microorganisms, semi-synthetic substances derived therefrom and totally synthetic substances. Of these compounds, examples of preferred compounds include pravastatin, lovastatin, simvastatin, fluvastatin, rivastatin and atorvastatin. Pravastatin is disclosed in Japanese Patent Publication No. Sho 61-13699 and in U.S. Pat. Nos. 4,346,227 and 4,448,979, and its formula (as the sodium salt) is sodium 1,2,6,7,8,8a-hexahydro-6,8-tetrahydroxy-2-methyl-1-naphthaleneheptanoate. Lovastatin is disclosed in Japanese Patent Kokai Application No. Sho 58-16875 and in European Patent No. 22 478, and its formula is 6-{2-[1,2,6,7,8,8a-hexahydro-8-(2-methylbutyryloxy)-2,6-dimethyl-1-naphthyl]ethyl}tetrahydro-4-hydroxy-2H-pyran-2-one. Simvastatin is disclosed in Japanese Patent Kokai Application No. Hei 1-1476 and in European Patent No. 33 538, and its formula is 6-{2-1,2,6,7,8,8a-hexahydro-8-(2,2-dimethylbutyloxy)-2,6-dimethyl-1-naphthyl] ethyl}tetrahydro-4-hydroxy-2H-pyran-2-one. Fluvastatin is disclosed in Japanese Patent Publication No. Hei 2-46031 and in U.S. Pat. No. 4,739,073, and its formula (as the sodium salt) is sodium 7-[3-(4-fluoro-phenyl)-1-methylethyl)-1H-indol-2-yl)-3,5-dihydroxy-6-heptanoate. Rivastatin is disclosed in Japanese Patent Kokai Application No. Hei 1-216974 and in U.S. Pat. Nos. 5,006,530, 5,169, 857 and 5,401,746, and its formula (as the sodium salt) is sodium 7-(4-fluorophenyl)-2,6-diisopropyl-5-methoxymethylpyridin-3-yl)-3,5-dihydroxy-6-heptanoate.

Atorvastatin is disclosed in Japanese Patent Kokai Application No. Hei 3-58967 and in U.S. Pat. No. 5,273,995, and its formula is 2-(4-fluoro-phenyl)-5-(1-methylethyl)-3-phenyl-4-(phenylcarbamoyl)-1H-pyrrole-1-(2,4-dihydroxyhexanoic) acid.

The insulin sensitizer, the other active ingredient of the invention, may also be referred to as an insulin resistance-improving agent, and was originally used for the prevention and/or treatment of diabetes. The term embraces a wide variety of compounds, typically thiazolidinedione compounds, oxazolidinedione compounds and oxathiadiazole compounds.

These compounds are disclosed in, for example, Japanese Patent Kokai Applications No. Hei 4-69383 and Hei 7-330728, WO 89/08651, WO 91/07107, WO 92/02520, WO 94/01433, and U.S. Pat. Nos. 4,287,200, 4,340,605, 4,438,141, 4,444,779, 4,461,902, 4,572,912, 4,687,777, 4,703,052, 4,725,610, 4,873,255, 4,897,393, 4,897,405, 4,918,091, 4,948,900, 5,002,953, 5,061,717, 5,120,754, 5,132,317, 5,194,443, 5,223,522, 5,232,925, 5,260,445 and European Patent No. 676 398 etc. Of these, examples of preferred compounds include troglitazone, pioglitazone, englitazone, BRL-49653, 5-(4-{2-[1-(4-2'-pyridylphenyl)ethylideneaminooxy]ethoxyl}benzyl)-thiazolidine-2,4-dione (hereinafter "Compound A"), 5-{4-(5-methoxy-3-methylimidazo[5,4-b]pyridin-2-yl-methoxy)benzyl}thiazolidine-2,4-dione (preferably as its hydrochloride), 5-[4-(6-methoxy-1-methylbenzimidazol-2-ylmethoxy)benzyl]thiazolidine-2,4-dione, 5-[4-(1-methylbenzimidazol-2-ylmethoxy)benzyl]thiazolidine-2,4-dione and 5-[4-(5-hydroxy-1,4,6,7-tetramethyl-benzimidazol-2-ylmethoxy)benzyl]thiazolidine-2,4-dione. Troglitazone is disclosed in Japanese Patent Publication No. Hei 2-31079 and in U.S. Pat. No. 4,572,912, and its formula is 5-{4-[(6-hydroxy-2,5,7,8-tetramethyl-chroman-2-yl)methoxy]benzyl}-2,4-thiazolidinedione. Pioglitazone is disclosed in Japanese Patent Publication No. Sho 62-42903 and No. Hei 5-66956 and in U.S. Pat. Nos. 4,287,200, 4,340,605, 4,438,141, 4,444,779 and 4,725,610, and its formula is 5-{4-[2-(5-ethylpyridin-2-yl)ethoxy]benzyl}-2,4-thiazolidinedione. Englitazone is disclosed in Japanese Patent Publication No. Hei 5-86953 and in U.S. Pat. No. 4,703,052, and its formula is 5-[3,4-dihydro-2-(phenylmethyl)-2H-benzo-pyran-6-ylmethyl]-2,4-thiazolidinedione. BRL-49653 is disclosed in Japanese Patent Kokai Application No. Hei 1-131169 and in U.S. Pat. Nos. 5,002,953, 5,194,443, 5,232,925 and 5,260,445, and its formula is 5-{4-[2-methyl-2-(pyridin-2-ylamino)ethoxy]benzyl}-2,4-thiazolidinedione. Compound A is described in European Patent No. 708 098. 5-{4-(5-Methoxy-3-methylimidazo[5,4-b]pyridin-2-ylmethoxy)benzyl}-thiazolidine-2,4-dione (and its hydrochloride) are disclosed in Japanese Patent Kokai Application No. Hei 7-330728 and in European Patent No. 676 398. The above compounds may be prepared as described in the prior art referred to above. 5-(4-(6-Methoxy-1-methylbenzimidazol-2-ylmethoxy)benzyl]thiazolidine-2,4-dione, 5-[4-(1-methylbenzimidazol-2-ylmethoxy)benzyl]thiazolidine-2,4-dione and 5-[4-(5-hydroxy-1,4,6,7-tetramethylbenz-imidazol-2-ylmethoxy)benzyl]thiazolidine-2,4-dione are disclosed in European Patent Application No. 96303940.9, and may be prepared as described hereafter.

The active ingredients used in the present invention comprise, first, one or more HMG-CoA reductase inhibitors and, second, one or more insulin sensitizers or insulin resistance-improving agents. According to the invention, a combination of the HMG-CoA reductase inhibitor and the insulin sensitizer exhibits a synergistic effect in comparison with the application of the respective components alone, as shown below. Interestingly, such synergism appears to occur even if the compounds of the two classes do not always exist simultaneously in the body. That is, the synergistic effect may be observed even when the concentration of one of the compounds of the two classes in the blood is less than that required by itself to exhibit any appreciable effect. Although it is a mere conjecture, it is thought that, when a compound of one of the two classes is received in the body and transported to a receptor, it actuates a "switch" in vivo. After some time, the level of the compound in the blood may have decreased to a value at which it seems that no further effect should be observed, but the "switch" may still be actuated, thus maintaining the preventive and/or therapeutic effect for arteriosclerosis and/or xanthoma inherent in the compounds of that class. When a compound of the other class is administered to a patient in this state, the effect on the prevention and/or treatment of arteriosclerosis and/or xanthoma may be combined with the effect resulting from the previous administration of the other compound, and the effects of the two compounds operate together in a favourable synergistic manner. It is, of course, obvious that it may well be convenient to administer the two compounds simultaneously in clinical practice. Therefore, the HMG-CoA reductase inhibitor and the insulin sensitizer may be administered together in the form of a combined preparation. Alternatively, if it is difficult to mix the two agents, either because of some incompatibility between them or for some other reason, for example problems in the mixing process, the two active agents may be administered separately in the form of single doses. As described above, since the compounds of the two classes exhibit together a synergistic effect, they may be administered almost simultaneously or at suitable intervals. The maximum interval acceptable for administering the compounds of the two classes in order to achieve the synergistic effect of the present invention may be confirmed by clinical practice or by experiments using animals.

The HMG-CoA reductase inhibitors and insulin sensitizers of the present invention may generally be administered orally. Accordingly, the compounds of the two classes may be separately prepared as two unit dosage forms or may be mixed physically to give a single unit dosage form. Examples of such formulations include, for example, powders, granules, tablets or capsules. These pharmaceutical formulations may be produced by conventional means well known in the pharmaceutical field.

In the present invention, the individual doses of the HMG-CoA reductase inhibitors and the insulin sensitizers and the ratio of between the amounts of the HMG-CoA reductase inhibitors and the insulin sensitizers may vary widely, depending upon the activity of each compound and upon other factors, such as the condition, age and body weight of the patient. For example, in the case of the insulin sensitizer, the potency of BRL-49653 is about 100 times higher than that of troglitazone in vivo in a diabetic animal model, allowing the dose of these two compounds to differ in theory by around two orders of magnitude, and, in practice, to differ by around one order of magnitude. The dose of each of the HMG-CoA reductase inhibitors and the insulin sensitizers, where they are used in the treatment of arteriosclerosis or xanthoma, would normally be expected to be lower than that which is used when the two compounds are employed separately for their original uses, that is as antihyperlipidemic and antidiabetic agents. Their doses are further lowered to some extent by the synergistic effect due to the combination of the compounds of the two classes. For example, where pravastatin and troglitazone are used in accordance with the invention, their daily doses are preferably within the range of from 1 mg to 40 mg and from 1 mg to 500 mg, respectively, as compared with doses of from 5 mg to 80 mg and from 10 mg to 1000 mg, respectively, where the compounds are employed for their original uses as antihyperlipidemic and antidiabetic agents.

More generally, although, as remarked above, the dose of the HMG-CoA reductase inhibitors and the insulin sensitizers according to the invention may widely vary, the daily dose is normally within the range of from 0.01 mg to 40 mg, preferably from 1 mg to 40 mg, and from 0.05 mg to 500 mg, preferably from 1 mg to 500 mg, respectively.

The ratio between the compounds of these the two classes may also vary widely, however, we prefer that the ratio of the HMG-CoA reductase inhibitor to the insulin sensitizer should be within the range of from 1:200 to 200:1 by weight, preferably from 1:100 to 10:1 and more preferably from 1:50 to 5:1 by weight.

The HMG-CoA reductase inhibitor and the insulin sensitizer in accordance with the invention are preferably administered simultaneously or almost simultaneously at a daily dose as described above, and may be administered as a single dose or as divided doses.

The compounds and compositions of the present invention can be administered in various forms, depending on the disease or disorder to be treated and the age, condition and body weight of the patient, as is well known in the art. For example, where the compounds or compositions are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent.

Examples of vehicles which may be employed include: organic vehicles including: sugar derivatives, such as lactose, sucrose, glucose, mannitol and sorbitol; starch derivatives, such as corn starch, potato starch, α-starch, dextrin and carboxymethylstarch; cellulose derivatives, such as crystalline cellulose, low-substituted hydroxypropylcellulose, hydroxypropylmethylcellulose, carboxymethylcellulose, calcium carboxymethylcellulose and internally bridged sodium carboxymethylcellulose; gum arabic; dextran; Pullulane; and inorganic vehicles including silicate derivatives, such as light silicic anhydride, synthetic aluminum silicate and magnesium aluminate metasilicate; phosphates, such as calcium phosphate; carbonates, such as calcium carbonate; and sulfates, such as calcium sulfate.

Examples of lubricants which may be employed include: stearic acid; metal stearates, such as calcium stearate and magnesium stearate; talc; colloidal silica; waxes, such as beeswax and spermaceti wax; boric acid; adipic acid; sulfates, such as sodium sulfate; glycol; fumaric acid; sodium benzoate; DL-leucine; fatty acid sodium salts; lauryl sulfates, such as sodium lauryl sulfate and magnesium lauryl sulfate; silicates, such as silicic anhydride and silicic acid hydrate; and the aforementioned starch derivatives.

Examples of binders which may be employed include: polyvinylpyrrolidone; macrogol; and the same compounds as are mentioned above for the vehicles.

Examples of disintegrators which may be employed include: the same compounds as are mentioned above for the vehicles; and chemically modified starches and celluloses, such as sodium crosscarmellose, sodium carboxymethylstarch and bridged polyvinylpyrrolidone.

Examples of stabilizers which may be employed include: paraoxybenzoates, such as methylparabene and propylparabene; alcohols, such as chlorobutanol, benzyl alcohol and phenylethyl alcohol; benzalkonium chloride; phenols, such as phenol and cresol; thimerosal; dehydroacetic acid; and sorbic acid.

Examples of corrigents which may be employed include: sweetening agents, acidifiers and spices.

The present invention is further illustrated by the following Examples, which demonstrate the enhanced activity achieved by the synergistic combination of the present invention. In addition, the subsequent Formulations illustrate the pharmaceutical formulations which may be prepared and the Preparations illustrate the preparation of certain of the insulin sensitizers used in the present invention.

EXAMPLE 1

WHHL rabbits [2-3 months of age, the Watanabe heritable hyperlipidemic rabbit described in Biochimica et Biophysica Acta, 960, 294–302 (1988)] were randomly assigned to a control group (7 animals, group A), a group receiving pravastatin alone (5 animals, Group B), a group receiving troglitazone alone (7 animals, Group C), and a group receiving a combination of both active substances (6 animals, Group D). Pravastatin was administered orally by gavage at a dose of 50 mg/kg/day once-daily and troglitazone was given in the diet, containing 100 mg/kg of the substance for 32 weeks. The ingested amount was limited to a daily 120 g per rabbit. Blood was withdrawn from the animal immediately before starting the study and 4, 8, 12, 16, 20, 24, 28 and 32 weeks after starting the study and the total cholesterol levels (mg/dl) were determined for each blood sample. The levels are reported as a percentage (%) of the levels measured immediately before starting the study. The results are shown in Table 1. The animals were sacrificed and necropsied at week 32 to examine (a) the percent lesion area (%) in the total, thoracic or abdominal portion of the aorta; (b) the stenosis (%) of the coronary arteries and (c) the incidence (%) of xanthoma in the digital joints.

The results are shown in Table 2, Table 3 and Table 4. The values actually measured are represented as an average value±standard error in those Tables.

TABLE 1

| Week | Group A | Group B | Group C | Group D |
|---|---|---|---|---|
| 0 | (981 ± 25)* | (988 ± 19)* | (967 ± 54)* | (988 ± 47)* |
|   | (100) | (100) | (100) | (100) |
| 4 | 103 | 87 | 88 | 70 |
| 8 | 102 | 87 | 89 | 69 |
| 12 | 98 | 81 | 78 | 66 |
| 16 | 98 | 81 | 83 | 65 |
| 20 | 90 | 75 | 72 | 57 |
| 24 | 83 | 68 | 73 | 59 |
| 28 | 79 | 68 | 77 | 61 |
| 32 | 76 | 60 | 76 | 61 |

*actually measured volume (mg/dl)

TABLE 2

| | Lesion area (%) | | |
| --- | --- | --- | --- |
| | Total aorta | Thoracic aorta | Abdominal aorta |
| Group A | 65.7 ± 3.9 | 79.3 ± 5.4 | 29.9 ± 4.4 |
| Group B | 53.8 ± 8.2 | 64.6 ± 10.4 | 28.2 ± 8.1 |
| Group C | 51.7 ± 7.7 | 57.9 ± 9.9 | 27.6 ± 7.0 |
| Group D | 41.3 ± 7.7* | 44.0 ± 9.5* | 21.3 ± 7.3* |

*p < 0.05. Significantly different against the control group under the Mann-Whitney's U-Test.

TABLE 3

| | | Coronary stenosis (%) | | | | | |
| --- | --- | --- | --- | --- | --- | --- | --- |
| Group | Number of animals | MLC | MRC | LAD | LCX | RCA | LSP |
| A | 3 | 61 | 79 | 24 | 47 | 13 | 40 |
| B | 2 | 71 | 81 | 16 | 34 | 18 | 9 |
| C | 3 | 59 | 83 | 11 | 39 | 7 | 31 |
| D | 3 | 39 | 81 | 3 | 23 | 1 | 27 |

MLC: main left coronary artery
MRC: main right coronary artery
LAD: left anterior descending artery
LCX: left circumflex artery
RCA: right coronary artery
LSP: left septal artery

TABLE 4

| | Incidence of xanthoma (%) | | |
| --- | --- | --- | --- |
| | Foreleg | Hind leg | Total |
| Group A | 100(14/14) | 100(14/14) | 100(28/28) |
| Group B | 80(8/10) | 80(8/10) | 80(16/20) |
| Group C | 86(12/14) | 29(4/14) | 57(16/28) |
| Group D | 0(0/12) | 0(0/12) | 0(0/24) |

As can be seen from the above example, no significant difference was observed in the change of plasma cholesterol levels at 32 weeks after administration between group D (which received a combination of both agents) and group B (which received pravastatin alone). In contrast, there was observed clear synergism in the percent lesion area ratio (lesion area/total artery area in %) by comparing Group D (combination treatment) with Groups B and C (single agent treatment) as shown above. Synergism was observed in preventing coronary stenosis in respect of the left anterior descending artery, the left circumflex artery and the right coronary artery. Development of xanthoma on the digital joints was entirely prevented in Group D, thus demonstrating clear synergism.

Thus, although the levels of plasma cholesterol revealed no significant difference when comparing the groups administered a combination of an HMG-CoA reductase inhibitor and an insulin sensitizer with the groups administered the active agent alone, the combination of both active agents synergistically prevented progression of the arteriosclerosis, particularly of the thoracic aorta. These results could not be imagined from the state of the prior art.

EXAMPLE 2

Male WHHL rabbits (2-3 months of age) which showed almost no arterial lesions were randomly assigned to a control group (7 animals, Group A), to a group subjected to oral administration of pravastatin alone (6 animals, 50 mg/kg, group B), to a group subjected to oral administration of pioglitazone alone (7 animals, 20 mg/kg, Group C), to a group subjected to oral administration of 5-(4-{2-|1-(4-2'-pyridyl-phenyl)ethylideneaminooxy|ethoxy}benzyl)thiazolidine-2,4-dione (hereinafter Compound A, as described in EP 708 098, 7 animals, 10 mg/kg, Group D), to a group subjected to oral administration of a combination of pravastatin and pioglitazone (6 animals, 50+20 mg/kg, Group E), and to a group subjected to oral administration of combination of pravastatin and Compound A (7 animals, 50+10 mg/kg, Group F).

Each test compound was administered for eight months to the rabbits in the form of an aqueous suspension (0.5% carboxymethylcellulose added). In the control group, a 0.5% carboxymethylcellulose solution only was administered. One month after the start of administration and thereafter, it was observed that the serum cholesterol in Groups B, E and F was maintained at a lower level than that of the control group, and a 22 to 34% reduction of the serum cholesterol levels were observed in those groups. However, no reduction of the serum cholesterol levels were observed in Groups C and D.

The percentage area covered by lesions at the aortic arch and over the whole aorta are shown in Table 5.

TABLE 5

| | Lesion Area (%) | |
| --- | --- | --- |
| Group | Aortic Arch | Total Aorta |
| A | 82 ± 5(100) | 59 ± 5(100) |
| B | 59 ± 11(72) | *35 ± 6(70) |
| C | 72 ± 10(88) | 54 ± 8(108) |
| D | 63 ± 9(77) | 38 ± 8(76) |
| E | **43 ± 2(52) | *31 ± 4(62) |
| F | **33 ± 8(40) | **26 ± 5(52) |

The values actually measured are represented by the mean value plus or minus standard error. The numbers in parentheses represent the percentage lesion area against the control group.

*p<0.05, **p<0.01; significant difference against the control group under the [Mann-Whitney's U-Test A significant difference (p<0.05) was observed between Groups B and F, between Groups C and E and between Groups D and F at the aortic arch, and between Groups C and E over the total aorta.

The average thickening of intima in aorta was measured and the results are shown in Table 6.

TABLE 6

| | Average thickening of intima (µm) in aorta | |
| --- | --- | --- |
| Group | Aortic Arch | Total Aorta |
| A | 237 ± 63(100) | 154 ± 33(100) |
| B | 194 ± 42(82) | 126 ± 22(82) |
| C | 245 ± 37(103) | 177 ± 26(115) |
| D | 291 ± 51(123) | 162 ± 22(105) |
| E | 189 ± 29(80) | 118 ± 10(77) |
| F | 146 ± 36(62) | 94 ± 18(61) |

The values actually measured are represented as the mean value plus or minus a standard error (µm). The numbers in parentheses represent the percentage intimal thickening against the control group. A significant difference was observed between Groups D and F at the aortic arch, and between Groups C and E and between Groups D and F over the total aorta (p<0.05) under the Mann-Whitney's U-Test.

The average thickening of the intima is calculated by the cross-sectional area of the aortic tunica intima one section from the arch and two sections from the thoracic and abdominal portions, divided by the length of the tunica media.

A slight suppression of intimal thickening was observed in Group B, whilst no suppression of hypertrophy was observed in Groups C and D. The suppression of intimal thickening in Groups E and F was observed against that in Groups C and D.

The aortic cholesterol content was measured The tunica media and tunica intima at the aortic arch and at the thoracic and abdominal aorta were peeled away with tweezers and cut into pieces. The pieces were extracted with a 2:1 by volume mixture of chloroform and methanol.

The chloroform phase was separated and evaporated to dryness and the residue was dissolved in isopropanol. The total cholesterol and the free cholesterol were measured by a conventional enzymatic method.

The results are shown in Tables 7a and 7b.

TABLE 7a

| | Cholesterol Content of Aortic Arch | | |
|---|---|---|---|
| Group | Total | Free | Esterified |
| A | 27.1 ± 3.3(100) | 20.6 ± 2.9(100) | 6.5 ± 1.4(100) |
| B | 24.9 ± 5.2(92) | 18.6 ± 4.4(90) | 6.4 ± 1.1(98) |
| C | 33..5 ± 4.5(124) | 26.9 ± 2.3(131) | 6.6 ± 2.7(102) |
| D | 21.4 ± 0.7(79) | 16.9 ± 1.8(82) | 4.5 ± 1.3(69) |
| E | 24.3 ± 2.8(90) | 18.0 ± 2.4(87) | 6.3 ± 1.8(97) |
| F | 18.5 ± 2.6(68) | 16.3 ± 2.5(79) | 2.2 ± 0.8(34)* |

TABLE 7b

| | Cholesterol level of Thoracic and Abdominal Aorta | | |
|---|---|---|---|
| Group | Total | Free | Esterified |
| A | 20.1 ± 2.3(100) | 14.8 ± 2.3(100) | 5.3 ± 1.7(100) |
| B | 17.2 ± 1.6(86) | 12.5 ± 1.3(84) | 4.7 ± 0.7(89) |
| C | 33.9 ± 7.3(169) | 23.4 ± 3.8(158) | 10.5 ± 3.8(198) |
| D | 14.0 ± 1.7(70) | 9.2 ± 1.0(62) | 4.9 ± 0.9(92) |
| E | 11.7 ± 2.2(58)* | 8.5 ± 1.9(57) | 3.2 ± 0.8(60) |
| F | 11.7 ± 1.7(58)** | 7.8 ± 1.2(53)* | 3.9 ± 0.7(74) |

*$p < 0.05$;
**$p < 0.02$.

Data are expressed by the mean plus or minus standard error (mg/g tissue). The values in parentheses indicate the percentage against the control. A significant difference against the control group was observed by the unpaired student t-test:

As is clear from Table 7, the total cholesterol levels of the thoracic and abdominal aorta are lower in Groups E and F than in Groups B, C and D. There was no clear cut trend between the free and esterified cholesterol levels. The results are similar to those of the rate of lesion area.

The incidence and the degree of xanthoma of the four legs were measured. The results are shown in Table 8.

TABLE 8

| | Incidence | | | Distribution of severity of lesion | | | | Frequency of massive |
|---|---|---|---|---|---|---|---|---|
| Group | Forelegs | Hindlegs | Total | − | + | ++ | +++ | xanthoma |
| A | 100 (14/14) | 100 (14/14) | 100(28/28) | 0 | 12 | 10 | 6 | 57 |
| B | 100[1) (12/12) | 75*[3)*4) (9/12) | 88*[7)*8) (21/24) | 3 | 11 | 8 | 2 | 42*[11) |
| C | 100 (14/14) | 86*[3) (12/14) | 93*[9) (26/28) | 2 | 7 | 11 | 8 | 68*[12) |
| D | 93*[2) (13/14) | 86*[6) (12/14) | 89*[10) (25/28) | 3 | 19 | 6 | 0 | 21**[13) |
| E | 92 (11/12) | 33**[3)*5) (4/12) | 63**[7)*9) (15/24) | 9 | 9 | 5 | 1 | 25*[12) |
| F | 50*[1)*2) (7/14) | 7**[4)*6) (1/14) | 29**[8)*10) (8/28) | 20 | 8 | 0 | 0 | 0**[11)*13) |

Data in parentheses express the number of injured legs/number of examined legs.
The severity of xanthoma was evaluated according to the following criteria:
(−) no lesions
(+) slight lesion
(++) moderate lesion
(+++) severe lesion
*$p < 0.05$,
**$p < 0.01$. Significantly different from the control group.
*1)$p < 0.01$. Significantly different between Groups B & F.
*2)$p < 0.05$. Significantly different between Groups D & F.
*3)$p < 0.05$. Significantly different between Groups B & E.
*4)$p < 0.01$. Significantly different between Groups B & F.
*5)$p < 0.01$. Significantly different between Groups C & E.
*6)$p < 0.01$. Significantly different between Groups D & F.
*7)$p < 0.05$. Significantly different between Groups B & E.
*8)$p < 0.01$. Significantly different between Groups B & F.
*9)$p < 0.01$. Significantly different between Groups D & F.
*10)$p < 0.01$. Significantly different between Groups D & F.

TABLE 8-continued

|  | Incidence | | | Distribution of severity of lesion | | | | Frequency of massive xanthoma |
|---|---|---|---|---|---|---|---|---|
| Group | Forelegs | Hindlegs | Total | − | + | ++ | +++ | |

*[11]*$p < 0.01$. Significantly different between Groups B & F.
*[12]*$p < 0.01$. Significantly different between Groups C & E.
*[13]*$p < 0.01$. Significantly different between Groups D & F.

As is clear from Table 8, the control group showed a 100% incidence of xanthoma in all of the forelegs and hindlegs. Groups B, C and D showed a slightly less frequent incidence of xanthoma. Groups E and F, the combination groups, showed a significantly lower frequency of incidence of xanthoma. The trend is similar in the frequency of massive xanthoma, wherein the Groups E and F showed quite a low frequency of, or no occurrence of, xanthoma, as opposed to Groups A to D.

The net results are that the two combinations of pravastatin, a HMG-CoA reductase inhibitor, and one of the thiazolidinedione insulin sensitizers exhibit synergistic effects on the treatment of atherosclerosis and on the occurrence of xanthoma.

EXAMPLE 3

Synergism of HMG CoA reductase inhibitors and thiazolidinedione insulin sensitizers were examined on the regression of established atherosclerotic lesions in the cholesterol-fed rabbit model.

Male New Zealand white rabbits (5 months of age) were fed for two months with a 2% cholesterol diet, at the end of this time, the serum cholesterol of the rabbits increased to 1,100–4,100 mg/dl.

The rabbits were grouped randomly (3–9 animals per group) and the test samples were administered orally for two months, while they were fed with a normolipidaemic diet. The dosage of the test samples was: in the case of pravastatin alone, 3 mg/kg or 5 mg/kg; in the case of fluvastatin alone, 0.8 mg/kg or 1.5 mg/kg; in the case of troglitazone alone, 10 mg/kg; in the case of Compound A alone, 2.5 mg/kg. In the case of combination groups, the dosage was: pravastatin 3 mg/kg+troglitazone 10 mg/kg; pravastatin 5 mg/kg:+ Compound A 2.5 mg/kg; fluvastatin 0.8 mg/kg+troglitazone 10 mglkg; and fluvastatin 1.5 mg/kg+Compound A 2.5 mg.

The results are shown in terms of the percentage of lesion area in the thoracic aorta.

As is clear from Table 9, each of the HMG CoA reductase inhibitors or the thiazolidinedione insulin sensitizers alone showed no or little reduction of the lesions, whilst all of the combination groups of the two components showed a synergistic reduction of the lesions.

EXAMPLE 4

Synergism of HMG CoA reductase inhibitors and thiazolidinedione insulin sensitizers was examined by another regression model, i.e. the regression of preformed atherosclerosis in hamsters. Male $F_1b$ hamsters (weight about 130 g.) were given a diet containing 0.05% cholesterol for 13 weeks. They were grouped randomly (2–7 animals per group), and then the test samples were administered for 4 weeks while the hamsters were given a normolipidaemic diet. Pravastatin and fluvastatin were mixed with drinking water at the dose of 3 mg/kg and 1.5 mg/kg, respectively, while troglitazone was mixed with the diet at the dose of 30 mg/kg or 100 mg/kg.

In the case of the combination groups, the dosage was 3 mg/kg+30 mg/kg or 3 mg/kg+100 mg/kg for the pravastatin+troglitazone group, and 1.5 mg/kg+30 mg/kg for the fluvastatin+troglitazone group.

The arterial lesions were evaluated by the extent of the area stained with Oil Red O (ORO), as described in Atherosclerosis, 114, 19–28 (1995). Namely, the aortic arch was stained with ORO to prepare en face specimens. The percentage area which was positive to the ORO stain over the whole area was measured to represent the degree of aortic lesion.

After the treatment, the total serum cholesterol and triglyceride level did not significantly differ among the groups.

The results are shown in Table 10.

TABLE 9

| Compound | Dosage (mg/kg) | Number of animals | Rate of lesion area (%) |
|---|---|---|---|
| Control | (none) | 3 | 29 ± 20 (100) |
| Pravastatin | 3 | 5 | 30 ± 12 (103) |
|  | 5 | 5 | 23 ± 9 (79) |
| Fluvastatin | 0.08 | 5 | 27 ± 9 (93) |
|  | 1.5 | 5 | 39 ± 16 (134) |
| Troglitazone | 10 | 6 | 23 ± 7 (79) |
| Compound A | 2.5 | 3 | 27 ± 7 (93) |
| Pravastatin + Troglitazone | 3 + 10 | 9 | 19 ± 5 (66) |
| Pravastatin + Compound A | 5 + 2.5 | 5 | 9 ± 5 (31) |
| Fluvastatin + Troglitazone | 0.8 + 10 | 7 | 18 ± 11 (62) |
| Fluvastatin + Compound A | 1.5 + 2.5 | 5 | 18 ± 9 (62) |

The values actually measured are expressed by the mean value±standard error. The figures in parentheses represent percent reduction of lesions against the control group.

TABLE 10

| Compound | Dosage (mg/kg) | No of Animals | Stained Area ORO (%) | % of Control |
|---|---|---|---|---|
| Control | 0 | 5 | 1.82 ± 0.44 | 100 |
| Pravastatin | 3 | 5 | 1.93 ± 0.33 | 106 |
| Fluvastatin | 1.5 | 6 | 1.74 ± 0.49 | 96 |
| Troglitazone | 30 | 7 | 1.99 ± 0.40 | 109 |
| Troglitazone | 100 | 7 | 1.05 ± 0.64 | 58 |
| Pravastatin + Troglitazone | 3 30 | 5 | 1.28 ± 0.49 | 70 |
| Pravastatin + Troglitazone | 3 100 | 4 | 0.63 ± 0.08 | 35 |
| Fluvastatin + Troglitazone | 1.5 30 | 2 | 0.73 | 40 |

There was a significant difference ($p<0.05$) between the control and the group receiving pravastatin+troglitazone 3 mg/kg+100 mg/kg and between the group receiving pravastatin alone and the group receiving pravastatin+ troglitazone 3 mg/kg+100 mg/kg.

As is clear from Table 10, no regression of aortic lesions was observed in the groups administered pravastatin, fluvastatin or troglitazone (30 mg/kg) alone, although regression was observed with troglitazone alone at the dosage of 100 mg/kg.

In the case of the combination of pravastatin and troglitazone, regression was observed, with a dose-dependent trend based on troglitazone. In the case of the combination of fluvastatin and troglitazone a similar synergistic regression of aortic lesions was observed.

In summary, it can be concluded that the combination of a HMG-CoA reductase inhibitor and a thiazolidinedione insulin sensitizer exhibit, as a class, both preventative and curative effects on atherosclerosis and on xanthoma.

PREPARATION 1

5-[4-(1-Methylbenzimidazol-2-ylmethoxy)benzyl]-thiazolidine-2,4-dione

1(a) Methyl 4-nitrophenoxyacetate

A mixture of 56 g of 4-nitrophenol, 90 g of methyl bromoacetate, 100 g of potassium carbonate and 500 ml of dimethylformamide was stirred at room temperature for 2 days. At the end of this time, the solvent was removed by distillation under reduced pressure. The resulting residue was mixed with water and the aqueous mixture was extracted with ethyl acetate. The extract was washed with water and dried over anhydrous sodium sulfate, after which the solvent was removed by distillation under reduced pressure. The resulting residue was triturated with hexane to give 63.3 g of the title compound, melting at 98–99° C.

1(b) Methyl 4-aminophenoxyacetate

A solution of 30.8 g of methyl 4-nitrophenoxyacetate [prepared as described in step (a) above] in 500 ml of methanol was shaken in an atmosphere of hydrogen and in the presence of 5.0 g of 10 w/w palladium-on-charcoal for 6 hours. At the end of this time, the reaction mixture was filtered and the filtrate was concentrated by evaporation under reduced pressure, to give 25.8 g of the title compound having an Rf value=0.79 (on thin layer chromatography on silica gel; developing solvent: ethyl acetate).

1(c) Methyl 4-(2-bromo-2-butoxycarbonylethyl-1-yl)-phenoxyacetate 98 g of 47% w/W aqueous hydrobromic acid, followed by 33 ml of an aqueous solution containing 12.8 g of sodium nitrite, were added to a solution of 25.8 g of methyl 4-aminophenoxyacetate (prepared as described in step (b) above] in 263 ml of a 2:5 by volume mixture of methanol and acetone, whilst ice-cooling, and the resulting mixture was stirred, whilst ice-cooling, for 30 minutes. 18.2 g of butyl acrylate were then added, and the reaction mixture was stirred for a further 30 minutes, whilst ice-cooling. 3.2 g of copper(I) bromide were then added to the mixture, and the mixture was stirred overnight at room temperature. At the end of this time, the reaction mixture was freed from the solvent by distillation under reduced pressure, and the residue was mixed with an aqueous solution of sodium chloride. It was then extracted with ethyl acetate. The extract was washed with an aqueous solution of sodium chloride and dried over anhydrous sodium sulfate. On distilling off the solvent, there were obtained 51.7 g of the title compound having an Rf value=0.46 (on thin layer chromatography on silica gel; developing solvent: a 5:1 by volume mixture of hexane and ethyl acetate) as a crude product.

1(d) 5-[4-(Ethoxycarbonylmethoxy)benzyl]thiazolidine-2,4-dione

A mixture of 100 g of methyl 4-(2-bromo-2-butoxy-carbonylethyl-1-yl)phenoxyacetate [prepared as described in step (c) above], 22 g of thiourea and 200 ml of ethanol was heated under reflux for 2.5 hours, after which 2N aqueous hydrochloric acid was added to the reaction mixture. The mixture was then heated under reflux for 5 hours. At the end of this time, the reaction mixture was freed from the solvent by distillation under reduced pressure. The resulting residue was diluted with water and the aqueous mixture was extracted with ethyl acetate. The extract was dried over anhydrous magnesium sulfate, after which the solvent was removed by distillation under reduced pressure. The resulting residue was purified by column chromatography through silica gel using a 2:5 by volume mixture of ethyl acetate and hexane as the eluent, to give 19.4 g of the title compound, melting at 105°–106° C.

1(e) 5-[4-(1-Methylbenzimidazol-2-ylmethoxy)benzyl]-thiazolidine-2,4-dione

A mixture of 1.0 g of N-methyl-1,2-phenylenediamine, 3.8 g of 5-[4-(ethoxycarbonylmethoxy)benzyl]thiazolidine-2,4-dione [prepared as described in step (d) above], 20 ml of concentrated aqueous hydrochloric acid, 10 ml of 1,4-dioxane and 10 ml of water was heated under reflux for 5 hours. At the end of this time, the insoluble materials which had precipitated from the reaction mixture were collected by filtration and the precipitate thus obtained was dissolved in tetrahydrofuran. Water was then added to the solution. The resulting aqueous mixture was neutralized by adding sodium hydrogencarbonate and then extracted with ethyl acetate. The extract was washed with an aqueous solution of sodium chloride and dried over anhydrous sodium sulfate. The solvent was then removed by evaporation under reduced pressure, and the resulting residue was purified by column chromatography through silica gel using ethyl acetate and then ethanol as the eluent. The product was then recrystallized twice from a mixture of tetrahydrofuran and ethyl acetate, to give 1.3 g of the title compound, melting at 230°–231° C.

PREPARATION 2

5-[4-(6-Methoxy-1-methylbenzimidazol-2-ylmethoxy)-benzyl]thiazolidine-2,4-dione

2(a) 5-Methoxy-2-nitroaniline 70 ml of a 28% w/v methanolic solution of sodium methoxide were added at room temperature to a solution of 25 g. of 5-chloro-2-nitroaniline in 500 ml of 1,4-dioxane, and the resulting mixture was heated under reflux for 4 hours, after which the solvent was removed by distillation under reduced pressure. The resulting residue was diluted with water, and the resulting aqueous mixture was extracted with ethyl acetate. The extract was washed with a saturated aqueous solution of sodium chloride and dried over anhydrous sodium sulfate, after which the solvent was removed by distillation under reduced pressure. The resulting residue was purified by column chromatography through silica gel using a gradient elution method, with mixtures of ethyl acetate and hexane in ratios ranging from 1:4 to 1:2 by volume as the eluent, to give 16.3 g of the title compound, melting at 124°–128° C.

2(b) N-t-Butoxycarbonyl-5-methoxy-2-nitroaniline 25 g of di-t-butyl dicarbonate, 15 ml of pyridine and 0.6 g of 4-dimethylaminopyridine were added at room temperature to a solution of 16 g of 5-methoxy-2-nitro-aniline [prepared as described in step (a) above] in 500 ml of dehydrated tetrahydrofuran, and the resulting mixture was stirred for 2 hours. At the end of this time, the reaction mixture was freed from the solvent by distillation under reduced pressure, and the resulting residue was diluted with water. The resulting aqueous mixture was extracted with ethyl acetate. The extract was washed with a saturated aqueous solution of sodium chloride and dried over anhydrous sodium sulfate, after which the solvent was removed by distillation under reduced pressure. The resulting residue was purified by column chromatography through silica gel using a 1:10 by volume mixture of ethyl acetate and hexane as the eluent, to give 12.5 g of the title compound, melting at 112°–114° C.

2(c) N-t-Butoxycarbonyl-N-methyl-5-methoxy-2-nitroaniline

A solution of 49.6 g of N-t-butoxycarbonyl-5-methoxy-2-nitroaniline [prepared as described in step (b) above] in 300 ml of dehydrated dimethylformamide was added, whilst ice-cooling, to a suspension of 12.0 g of sodium hydride (as a 55% w/w dispersion in mineral oil) in 300 ml of dehydrated dimethylformamide, and the resulting mixture was stirred at room temperature for 30 minutes, after which 17.2 ml of methyl iodide were added at room temperature. The reaction mixture was stirred for 1 hour, after which it was allowed to stand overnight at room temperature. It was then concentrated to about one-fifth of its original volume by evaporation under reduced pressure. The concentrate was mixed with ice-water and the resulting aqueous mixture was extracted with ethyl acetate. The extract was washed with water and with a saturated aqueous solution of sodium chloride, in that order, after which it was dried over anhydrous sodium sulfate. On distilling off the solvent, there were obtained 52.1 g of the title compound, melting at 122°–124° C.

2(d) N-Methyl-5-methoxy-2-nitroaniline 750 ml of a 4N solution of hydrogen chloride in 1,4-dioxane were added to 52 g of N-t-butoxycarbonyl-N-methyl-5-methoxy-2-nitroaniline [prepared as described in step (c) above] at room temperature, and the resulting mixture was stirred for 2 hours. At the end of this time, the reaction mixture was freed from the solvent by distillation under reduced pressure, and the resulting residue was mixed with water and ethyl acetate. The mixture was then neutralized by the addition of sodium hydrogencarbonate, after which it was extracted with ethyl acetate. The extract was washed with a saturated aqueous solution of sodium chloride and dried over anhydrous sodium sulfate. On distilling off the solvent, there were obtained 35.3 g of the title compound, melting at 107°–110° C.

2(e) 5-Methoxy-N-methyl-1,2-phenylenediamine 346 g of stannous chloride were added to a mixture of 35 g of N-methyl-5-methoxy-2-nitroaniline [prepared as described in step (d) above], 900 ml of t-butanol and 100 ml of ethyl acetate at room temperature, and the resulting mixture was stirred at 60° C. for 2 hours, after which 11 g of sodium borohydride were added in portions at 60° C. over a period of about 1 hour. The reaction mixture was then stirred at 60° C. for 3 hours, after which it was allowed to stand at room temperature for 2 days. It was then poured into ice-water and the aqueous mixture was neutralized by the addition of sodium hydrogencarbonate. The mixture was extracted with ethyl acetate, and the extract was washed with a saturated aqueous solution of sodium chloride and dried over anhydrous sodium sulfate. The solvent was removed from the mixture by distillation under reduced pressure, and the resulting residue was purified by column chromatography through silica gel using a 3:2 by volume mixture of ethyl acetate and hexane as the eluent, to give 21.9 g of the title compound having an Rf value=0.18 (on thin layer chromatography on silica gel; developing solvent: a 1:1 by volume mixture of ethyl acetate and hexane).

2(f) 5-(4-Methoxycarbonylmethoxybenzyl)-3-triphenylmethylthiazolidine-2,4-dione 126 g of cesium carbonate were added at room temperature to a solution of 120 g of 5-(4-hydroxy-benzyl)-3-triphenylmethylthiazolidine-2,4-dione in 2.5 litres of acetone, followed by 36 ml of methyl bromoacetate, and the resulting mixture was stirred for 1 hour. At the end of this time, the reaction mixture was freed from the solvent by distillation under reduced pressure, and the resulting residue was mixed with water. The aqueous mixture was then extracted with ethyl acetate. The extract was washed with water and then with a saturated aqueous solution of sodium chloride, after which it was dried over anhydrous magnesium sulfate. The solvent was removed by distillation under reduced pressure, after which 1 litre of diethyl ether was added to the oily residue. The mixture was then agitated ultrasonically for 10 minutes. The solid substance precipitated was collected by filtration, to give 126.3 g of the title compound, melting at 158°–162° C.

2(g) 5-(4-Methoxycarbonylmethoxybenzyl)thiazolidine-2,4-dione 1700 ml of acetic acid and then 400 ml of water were added at room temperature to a suspension of 344 g of 5-(4-methoxycarbonylmethoxybenzyl)-3-triphenylmethyl-thiazolidine-2,4-dione [prepared as described in step (f) above] in 400 ml of 1,4-dioxane and the resulting mixture was stirred for 5 hours at 80° C. At the end of this time, the reaction mixture was freed from the solvent by evaporation under reduced pressure, and the resulting residue was purified by column chromatography through silica gel using a 1:2 by volume mixture of ethyl acetate and hexane, a 2 1 by volume mixture of ethyl acetate and hexane and then ethyl acetate as eluents, to give 161.7 g of the title compound, melting at 100°–106° C.

2(h) 5-[4-(6-Methoxy-1-Methylbenzimidazol-2-Ylmethoxy)-Benzyl]Thiazolidine-2,4-Dione A mixture of 21.8 g of 5-methoxy-N-methyl-1,2-phenylenediamine [prepared as described in step (e) above], 63.4 g of 5-(4-methoxycarbonylmethoxybenzyl)-thiazolidin-2,4-dione [prepared as described in step (g) above], 250 ml of 1,4-dioxane and 750 ml of concentrated aqueous hydrochloric acid was heated under reflux for 60 hours. At the end of this time, the reaction mixture was cooled with ice, after which the solid matter was collected by filtration. 800 ml of a 5% w/v aqueous solution of sodium hydrogencarbonate was added to this matter, and the resulting mixture was stirred at room temperature for 2 hours. Insoluble materials were then collected by filtration and dissolved in a mixture of 1000 ml of dimethylformamide and 200 ml of methanol. The resulting solution was decolorized by treatment with activated charcoal, which was then removed by filtration. The filtrate was then concentrated by evaporation under reduced pressure to a volume of about 50 ml. The resulting concentrate was added to 750 ml of diethyl ether and the solution thus obtained was allowed to stand for 2 days. At the end of this time, the resulting precipitate was collected by filtration, to give 20.1 g of the title compound, melting at 267°–271° C. and having an Rf value=0.68 (on thin layer chromatography on silica gel; using a developing solvent of methylene chloride containing 5% v/v ethanol).

PREPARATION 3

5-[4-(5-Hydroxy-1,4,6,7-tetramethylbenzimidazol-2-yl-methoxy)Benzyl]thiazolidine-2,4-dione 3(a) Trimethylbenzoquinone A suspension of 25.6 g of ferric chloride in 50 ml of water was added at room temperature to a solution of 20 g of trimethylhydroquinone in 150 ml of acetone, and the resulting mixture was stirred for 1 hour, after which it was allowed to stand for 2 days. At the end of this time, it was concentrated to about one half of its original volume, and the concentrate was mixed with water. The resulting aqueous mixture was extracted with ethyl acetate, and the extract was washed with water and with a saturated aqueous solution of sodium chloride, in that order, after which it was dried over anhydrous sodium sulfate. The solvent was removed by distillation under reduced pressure, and the resulting residue was purified by column chromatography through silica gel, using a 1:6 by volume mixture of ethyl acetate and hexane as the eluent, to give 16.9 g of the title compound having an Rf value=0.48 (on thin layer chromatography on silica gel; developing solvent: a 1:6 by volume mixture of ethyl acetate and hexane).

3(b) 2,3,6-Trimethylbenzoauinone-4-oxime

A solution of 7.04 g of hydroxylamine hydrochloride in 30 ml of water was added at room temperature to a solution of 16.9 g of trimethylbenzoquinone [prepared as described in step (a) above] in 150 ml of methanol, and the resulting mixture was stirred for 2 hours, after which it was allowed to stand for 2 days. At the end of this time, the reaction mixture was diluted with 1000 ml of water. The precipitate which separated out was collected by filtration and recrystallized from a mixture of ethyl acetate and hexane, to give 11.2 g of the title compound, melting at 188°–190° C.

3(c) 4-Hydroxy-2,3,5-trimethylaniline 152 g of sodium hydrosulfite were added, whilst ice-cooling, to a mixture of 36.15 g of 2,3,6-trimethylbenzoquinone-4-oxime [prepared as described in step (b) above] and 880 ml of a 1N aqueous solution of sodium hydroxide, and the resulting mixture was stirred at room temperature for 1 hour, after which it was allowed to stand overnight. The reaction mixture was then poured into ice-water and the pH of the aqueous mixture was adjusted to a value of 4 to 5 by the addition of 5N aqueous hydrochloric acid, after which it was neutralized with sodium hydrogencarbonate. The mixture thus obtained was extracted with ethyl acetate. The extract was washed with a saturated aqueous solution of sodium chloride and dried over anhydrous sodium sulfate. The solvent was then removed by distillation under reduced pressure, after which the crystalline residue was triturated with diisopropyl ether and collected by filtration. On washing with diisopropyl ether, there were obtained 30.1 g of the title compound, melting at 131°–134° C.

3(d) N-t-Butoxycarbonyl-4-hydroxy-2,3,5-trimethylaniline 22.0 ml of triethylamine were added at room temperature to a solution of 20 g of 4-hydroxy-2,3,5-trimethylaniline [prepared as described in step (c) above] in 500 ml of tetrahydrofuran, followed by 34.6 g of di-t-butyl dicarbonate, and the resulting mixture was stirred for 6 hours, after which it was allowed to stand overnight. At the end of this time, the reaction mixture was freed from the solvent by distillation under reduced pressure, and the resulting residue was mixed with water. The resulting aqueous mixture was extracted with ethyl acetate. The extract was washed with a saturated aqueous solution of sodium chloride and dried over anhydrous sodium sulfate. The solvent was removed by distillation under reduced pressure, after which the crystalline residue was triturated with hexane, to give 31.9 g of the title compound, melting at 158°–161° C.

3(e) N-Methyl-4-hydroxy-2,3,5-trimethylaniline

A solution of 15 g of N-t-butoxycarbonyl-4-hydroxy-2,3, 5-trimethylaniline [prepared as described in step (d) above] in 200 ml of dehydrated tetrahydrofuran was added to a suspension of 6.8 g of lithium aluminum hydride in 300 ml of dehydrated tetrahydrofuran, whilst ice-cooling, and the resulting mixture was stirred at room temperature for 3 hours, after which it was heated under reflux for 2 hours. At the end of this time, a mixture of 10 ml of water and 30 ml of tetrahydrofuran was added to the reaction mixture in order to destroy any excess of lithium aluminum hydride. The reaction mixture was then stirred at room temperature for 1.5 hours, after which insoluble materials were filtered off with the aid of a Celite (trade mark) filter aid. These materials were washed with ethyl acetate, and the ethyl acetate washings were combined and dried over anhydrous sodium sulfate. The solvent was removed by distillation under reduced pressure, and the resulting residue was purified by column chromatography through silica gel using a 1:3 by volume mixture of ethyl acetate and hexane as the eluent, to give 5.1 g of the title compound, melting at 120°–122° C.

3(f) N-t-Butoxycarbonyl-N-methyl-4-hydroxy-2,3,5-trimethylaniline 5.0 ml of triethylamine and a solution of 7.92 g of di-t-butyl dicarbonate in 30 ml of tetrahydrofuran were added at room temperature to a solution of 5.0 g of N-methyl-4-hydroxy-2,3,5-trimethylaniline [prepared as described in step (e) above] in 70 ml of tetrahydrofuran, and the resulting mixture was stirred for 1 hour, after which it was allowed to stand overnight. At the end of this time, the reaction mixture was freed from the solvent by distillation under reduced pressure, and the resulting residue was mixed with water. The aqueous mixture was extracted with ethyl acetate. The extract was washed with water and with a saturated aqueous solution of sodium chloride, in that order, after which it was dried over anhydrous magnesium sulfate. After distilling off the solvent, the residual crystals were triturated with hexane and collected by filtration. There were obtained 7.35 g of the title compound, melting at 163°–166° C.

3(g) N-t-Butoxycarbonyl-N-methyl-4-acetoxy-2,3,5-trimethylaniline 5.64 ml of dehydrated triethylamine and 2.9 ml of acetyl chloride were added at room temperature to a solution of 7.2 g of N-t-butoxycarbonyl-N-methyl-4-hydroxy-2,3,5-trimethylaniline [prepared as described in step (f) above] in 100 ml of dehydrated tetrahydrofuran, and the resulting mixture was stirred for 1 hour, after which it was allowed to stand overnight. The reaction mixture was then diluted with water and the aqueous mixture was extracted with ethyl acetate. The extract was washed with water and with a saturated aqueous solution of sodium chloride, in that order, after which it was dried over anhydrous magnesium sulfate. The solvent was removed by distillation under reduced pressure, after which the residue was triturated with ice-cooled hexane to cause crystallization. The crystals were collected by filtration and washed with ice-cooled hexane to give 6.25 g of the title compound, melting at 103°–104° C.

3(h) N-Methyl-4-acetoxy-2,3,5-trimethylaniline Hydrochloride

A mixture prepared by adding 100 ml of a 4N solution of hydrogen chloride in 1,4-dioxane to 5.45 g of N-t-butoxycarbonyl-N-methyl-4-acetoxy-2,3,5-trimethylaniline [prepared as described in step (g) above] at room temperature was stirred for 3 hours. At the end of this time, the reaction mixture was freed from the solvent by distillation under reduced pressure, and the resulting residue was triturated with diisopropyl ether. The crystals thus obtained were collected by filtration, after which they were washed with diisopropyl ether to give 4.36 g of the title compound, melting at 172°–176° C.

3(i) N-Methyl-4-acetoxy-2,3,5-trimethyl-6-nitroaniline 4.3 g of N-methyl-4-acetoxy-2,3,5-trimethylaniline hydrochloride [prepared as described in step (h) above] were added to ice-cooled concentrated aqueous nitric acid, and the resulting mixture was stirred, whilst ice-cooling, for 10 minutes and then at room temperature for 10 minutes. At the end of this time, the reaction mixture was poured into ice-water and the aqueous mixture was neutralized by the addition of sodium hydrogencarbonate, after which it was extracted with ethyl acetate. The extract was washed with a saturated aqueous solution of sodium chloride and dried over anhydrous sodium sulfate. The solvent was then removed by distillation under reduced pressure, after which 50 ml of diisopropyl ether and 50 ml of hexane were added to the residue. The mixture was then agitated ultrasonically for 5 minutes. Insoluble precipitates were triturated with a 1:1 by volume mixture of diisopropyl ether and hexane. The resulting crystals were collected by filtration, after which they were washed with a 1:1 by volume mixture of diisopropyl ether and hexane to give 2.76 g of the title compound, melting at 143°–146° C.

3(j) 4-Acetoxy-N-Methyl-3,5,6-trimethyl-1,2-phenylenediamine

A solution of 2.65 g of N-methyl-4-acetoxy-2,3,5-trimethyl-6-nitroaniline [prepared as described in step (i) above] in a mixture of 20 ml ethanol and 20 ml of ethyl acetate was shaken at room temperature for 3.5 hours and then at 40° C. for 3 hours in an atmosphere of hydrogen and in the presence of 0.2 g of platinum oxide. At the end of this time, the reaction mixture was filtered to remove the platinum oxide and the filtrate was freed from the solvent by distillation under reduced pressure. The resulting residue was purified by column chromatography through silica gel, using a 1:1 by volume mixture of ethyl acetate and hexane as the eluent, to give 1.3 g of title compound, melting at 113°–116° C.

3(k) 5-[4-(5-Hydroxy-1,4,6,7-tetramethylbenzimidazol-2-ylmethoxy) benzyl]Thiazolidine-2,4-Dione A mixture of 1.0 g of 4-acetoxy-N-methyl-3,5,6-trimethyl-1,2-phenylenediamine [prepared as described in step (j) above], 2.7 g of 5-(4-methoxycarbonylmethoxybenzyl)thiazolidine-2,4-dione [prepared as described in step 2(g) of Preparation 2], 5 ml of 1,4-dioxane and 25 ml of concentrated aqueous hydrochloric acid was heated under reflux for 2 days. At the end of this time, the reaction mixture was added to ice-water and the resulting mixture was neutralized by the addition of sodium hydrogencarbonate. It was then extracted with ethyl acetate. The extract was washed with a saturated aqueous solution of sodium chloride and dried over anhydrous magnesium sulfate. The solvent was then removed by distillation under reduced pressure, after which the residue was purified by column chromatography through silica gel, using ethyl acetate as the eluent.

Fractions containing the title compound were collected and the solvent was removed by distillation under reduced pressure, to give a red residual oil. 150 ml of diethyl ether were added to the oil, and the mixture was agitated ultrasonically for 5 minutes. The precipitate which separated out was collected by filtration and dissolved in 300 ml of tetrahydrofuran. The resulting solution was concentrated to a volume of between about 10 ml and 20 ml by evaporation under reduced pressure. 200 ml of ethyl acetate were added to the concentrate, and the mixture was agitated ultrasonically for 20 minutes. The precipitate which separated out was collected by filtration, to give 0.52 g of the title compound, melting at 240°–244° C. and having an Rf value=0.44 (on thin layer chromatography on silica gel; developing solvent: ethyl acetate).

FORMULATION 1

Capsules 0.5 g of pravastatin sodium, 20 g of troglitazone, 1.5 g of crospovidone (polyvinylpyrrolidone disintegrator) and 0.2 g of sodium lauryl sulfate were blended. The mixture was divided between 100 empty capsules (number 1) to give 100 capsules, each containing 5 mg of pravastatin sodium and 200 mg of troglitazone.

FORMULATION 2

Tablets 40 g of a 5% w/v aqueous solution of hydroxypropylcellulose were added to a mixture of 5 g of pravastatin sodium, 2 g of Compound A, 24 g of hydroxypropylcellulose (low degree of substitution) and 86.9 g of lactose, and the resulting mixture was kneaded to give a composition. This composition was passed through a 10 mesh (Tyler standard mesh) screen and dried, after which it was passed through a 15 mesh (Tyler standard mesh) screen to give even sized grains. 11.9 g of the grains and 0.1 g of magnesium stearate were mixed and the mixture was made into tablets with a tableting machine, giving tablets of 6.5 mm diameter and 120 mg weight, each containing 5 mg of pravastatin sodium and 2 mg of Compound A.

We claim:

1. A method for the prevention or treatment of arteriosclerosis or xanthoma, which method comprises administering to a patient suffering from or susceptible to arteriosclerosis or xanthoma a first agent selected from the group consisting of HMG-CoA reductase inhibitors and a second agent selected from the group consisting of insulin sensitizers, said first and second agents being administered together in a synergistic mixture or individually in amounts and within such a period as to act synergistically together;

wherein said HMG-CoA reductase inhibitor is pravastatin and said insulin sensitizer is troglitazone.

2. The method of claim 1 wherein 0.01 mg to 40 mg of pravastatin and 0.05 mg to 500 mg of troglitazone are administered.

3. The method of claim 1 wherein 1 mg to 40 mg of pravastatin and 1 mg to 500 mg of troglitazone are administered.

4. The method of claim 2 wherein the ratio of amounts of pravastatin to troglitazone administered is 1:200 to 200:1.

5. The method of claim 4 wherein the ratio of amounts of pravastatin to troglitazone administered is 1:100 to 10:1.

6. The method of claim 5 wherein the ratio of amounts of pravastatin to troglitazone administered is 1:50 to 5:1.

* * * * *

UNITED STATES PATENT AND TRADEMARK OFFICE
CERTIFICATE OF CORRECTION

PATENT NO. : 5,798,375
DATED : August 25, 1998
INVENTOR(S) : Tsujita et al

It is certified that error appears in the above-identified patent and that said Letters Patent is hereby corrected as shown below:

Title Page, left column, [75] Inventors: after "Horikoshi" insert --Tokyo--; before "Takashi", insert --Masashi Shiomi--.

Title Page, right column, line 2: replace "5-69383" with --4-69383--.

Column 7, line 40: under the horizontal line ending TABLE 4, insert --The values in parentheses indicate the number of injured legs/the number of examined legs.--.

Column 8, line 43: before "Mann-Whitney's" delete "[".

Column 8, line 43: "A significant" is the beginning of a new paragraph.

Signed and Sealed this

Twenty-sixth Day of October, 1999

Attest:

Q. TODD DICKINSON

*Attesting Officer*     *Acting Commissioner of Patents and Trademarks*